(12) United States Patent
Shimokita

(10) Patent No.: US 9,119,640 B2
(45) Date of Patent: Sep. 1, 2015

(54) BONE CUTTING DEVICE

(75) Inventor: Ryo Shimokita, Hamamatsu (JP)

(73) Assignee: GENIAL LIGHT CO., LTD., Hamamatsu-shi (JP)

( * ) Notice: Subject to any disclaimer, the term of this patent is extended or adjusted under 35 U.S.C. 154(b) by 252 days.

(21) Appl. No.: 13/255,488

(22) PCT Filed: Mar. 9, 2010

(86) PCT No.: PCT/JP2010/053829
§ 371 (c)(1),
(2), (4) Date: Sep. 8, 2011

(87) PCT Pub. No.: WO2010/104053
PCT Pub. Date: Sep. 16, 2010

(65) Prior Publication Data
US 2011/0319879 A1     Dec. 29, 2011

(30) Foreign Application Priority Data
Mar. 10, 2009 (JP) .................. 2009-057042

(51) Int. Cl.
*A61B 18/20* (2006.01)
*A61B 17/16* (2006.01)
*A61B 18/22* (2006.01)
*A61B 19/00* (2006.01)

(52) U.S. Cl.
CPC ............ *A61B 17/1695* (2013.01); *A61B 18/22* (2013.01); *A61B 2017/1651* (2013.01); *A61B 2019/461* (2013.01)

(58) Field of Classification Search
CPC ..... A61N 1/375; A61N 1/3754; A61B 18/20; A61B 18/203
USPC ..................... 606/2–19; 607/88–94
See application file for complete search history.

(56) References Cited

U.S. PATENT DOCUMENTS

| 5,568,503 A * | 10/1996 | Omori ............................ 372/70 |
| 2007/0129711 A1 * | 6/2007 | Altshuler et al. ................. 606/9 |
| 2010/0049183 A1 | 2/2010 | Shimokita |

FOREIGN PATENT DOCUMENTS

| JP | 07016772 A | 1/1995 |
| JP | 07051287 A | 2/1995 |
| JP | 2007-526001 A | 9/2007 |
| WO | 2004-0107955 A2 | 12/2004 |
| WO | 2008-0102428 A1 | 8/2008 |

OTHER PUBLICATIONS

ISA Japanese Patent Office, International Search Report of PCT/JP2010/053829, Apr. 20, 2010, 2 pages.
R. Rohanizadeh et al., "Effects of Q-switched Nd: YAG Laser on Calcified Tissues," Lasers in Medical Science, Sep. 1999, vol. 14, No. 3.

* cited by examiner

*Primary Examiner* — Aaron Roane
(74) *Attorney, Agent, or Firm* — Alleman Hall McCoy Russell & Tuttle LLP

(57) ABSTRACT

To provide a bone cutting device capable of selectively cutting only a bone easily and quickly, the device of the present invention is adapted to cut a bone by irradiating with a laser beam and includes a light source for emitting a laser beam of 1000 to 1500 nm with a peak output of 10 to 70 W/cm$^2$.

8 Claims, 3 Drawing Sheets

PRIOR ART

BONE CUTTING DEVICE

TECHNICAL FIELD

This invention relates to a bone cutting device capable of selectively cutting only a bone easily and quickly.

BACKGROUND ART

Craniotomy is a fundamental technique of a neurosurgical operation and there can be listed, e.g., intracerebral hemorrhage and subarachnoid hemorrhage as a disease for which craniotomy is carried out.

A brain is made up of very soft tissue, and if a pressure in a degree of 200 mm $H_2O$ ($1.96 \times 10^3$ Pa) is applied, it will be destroyed. For this reason, in the case of cerebral hemorrhage, 25% of the brain dies within six hours after the onset thereof, and in the case of subarachnoid hemorrhage, 35% of the brain dies within 8 hours after the onset thereof. Therefore, the therapy thereof is very urgent.

Conventionally, in order to carry out craniotomy, as shown in FIG. 3, scalp S is first incised in an arc shape to exfoliate the incised skin flap and fascia and aponeurosis under the skin flap so that cranial bone BS is exposed, and then some small holes (burr holes) H are formed with a perforator which is a drill constructed for perforating cranial bone, and a bone piece is cut using an instrument (bone saw), which is a sort of an electromotive coping saw, along a dashed line D in the figure in a manner such that these holes are connected, and the bone piece is cut away from the cranial bone using a chisel or the like if necessary so as to form a bony window. It takes usually about 10 to 15 minutes to form such a bony window.

In this craniotomy operation, since the craniotomy is carried out using a mechanical instrument such as a drill, it is necessary to strongly fix a patient's head by exclusive braces. Moreover, the cranial bone is in a state of being very slippery with patient's body fluid such as blood, and yet in order not to wound other tissues (especially brain), it is necessary to perform an operation with the utmost caution.

And after craniotomy, a dura mater is incised to take an appropriate treatment according to a disease. That is, in the case of cerebral hemorrhage, an intracerebral hematoma is removed under a microscope, or in the case of subarachnoid hemorrhage, a metallic clip is placed over a root of cerebral aneurysm.

In order to close a bony window after a treatment to a brain, since a chipping allowance becomes large and a bone piece becomes small even if the removed bone piece is damaged slightly, there is a defection that a big crevice will arise between a bone flap and a cranial bone, therefore the bone piece will fall into the crevice. For this reason, the bone piece and the cranial bone are firmly fixed using a fastener formed in a plate made of expensive titanium, and the holes formed by a drill are also covered with a metal lid. However, since the bone piece is cut out using a chisel or the like, it is difficult to cut out the bone piece without damaging the bone piece. In the case where the damage of the cut-out bone piece is severe, it cannot be used as it is, and therefore bones of a pig, a cow, or the like are used as a substitute in many cases, and there may quite likely arise a rejection to these foreign matters.

Therefore, the conventional craniotomy is a highly invasive technique with a large physical burden, and dangers of a postoperative infectious disease and rejection are also high for a patient, and since the craniotomy operation covering a plurality of processes has many points in which a medical practitioner cannot but depend on experiences and institutions, physical and mental burdens are large for a medical practitioner and malpractice may be easily induced.

SUMMARY OF THE INVENTION

Technical Problem

Therefore, in consideration of the present status, the present invention has been made to provide a bone cutting device capable of selectively cutting only a bone easily and quickly.

Solution to Problem

As a result of wholehearted examination by the present inventor, it was found that, by irradiating with a laser beam of a specific wavelength with a specific peak output, only a bone can be selectively cut without wounding peripheral tissues even without providing a member for intercepting the laser beam between the bone and the peripheral tissues, and the present invention has been completed on the basis of the above knowledge. It is noted that a cartilage is also included in a "bone" in the present invention.

That is, a bone cutting device according to the present invention is a device for cutting a bone by irradiating with a laser beam and is characterized by including a light source for emitting a laser beam of 1000 to 1500 nm with a peak output of 10 to 70 $W/cm^2$.

With a device like this, by irradiating with a laser beam of 1000 to 1500 nm having a low absorptivity to water in a degree of 20 to 30% with a peak output of 10 to 70 $W/cm^2$, it is possible to selectively cut only a bone quickly at a speed in a degree of 2 mm/s without damaging peripheral tissues. For this reason, in the case of using the bone cutting device according to the present invention for craniotomy, it is possible to cut only a cranial bone quickly and take it off without wounding a brain only by one process of irradiation with a laser beam without perforating the cranial bone after incision of a scalp.

Moreover, if a bone to be cut is irradiated with a laser beam of 1000 to 1500 nm with a peak output of 10 to 70 $W/cm^2$, since the output of the laser beam after penetrating the bone is degraded to a degree of about 30 $W/cm^2$ or lower, the peripheral tissues are not damaged at all. For this reason, it is not necessary at all to provide a member for intercepting the laser beam between the bone and the peripheral tissues.

Moreover, in the craniotomy using the bone cutting device according to the present invention, even if a patient's head is not firmly fixed as in the conventional manner, a bone piece can be cut out safely and precisely.

Further, since a bone is cut by irradiating with a laser beam, a chipping allowance is very slight and carbonization of the cut-out bone piece is suppressed and physical breakage and deterioration are also little. For this reason, it is possible to re-join the cut-out bone piece as it is to the cut position even without using a fastener or the like.

Therefore, the craniotomy using the bone cutting device according to the present invention is by far less invasive with a light physical burden for a patient and dangers of a postoperative infectious disease and the rejection are also low, as compared to the conventional craniotomy using a mechanical instrument such as a drill, an electromotive coping saw, a chisel or the like. Also, since the craniotomy can be carried out with reduced induction factors of malpractice, physical and mental burdens for a medical practitioner can be also remarkably reduced.

Moreover, the light source is preferably a fiber laser. The fiber laser includes a fiber per se as a laser medium by adding a rare earth metal to an optical fiber, and by using the optical fiber as it is wound, space required for laser oscillation is remarkably reduced while an optical path length is kept remaining as it is.

Furthermore, in order to suppress thermal denaturation of a bone more effectively, it is preferable to include a jet part of inactive gas such as nitrogen gas.

In addition, in order to precisely control a focal position of a laser beam, it is preferable to include a distance sensor.

It is noted that the use of the bone cutting device according to the present invention is not limited to craniotomy and it may be applicable to any use as long as a process of cutting a bone is included and it may be applicable to any use other than that in a medical field.

Advantageous Effects of Invention

Thus, according to the present invention, since a bone can be cut by low invasive means, a physical burden for a patient can be remarkably reduced and a danger of occurrence of a postoperative infectious disease can be also reduced. Further, since damage and deterioration of a bone piece are little, it is possible to re-join the bone piece to the cut position even without using a fastener or the like. In addition, the burden of a bone cutting operation for a medical practitioner can be also remarkably reduced. Also, according to the present invention, since it is possible to cut a bone quickly, it is extremely superior in an urgent situation.

DESCRIPTION OF THE EMBODIMENTS

One embodiment of the present invention is described below with reference to the drawings.

Figure 1:
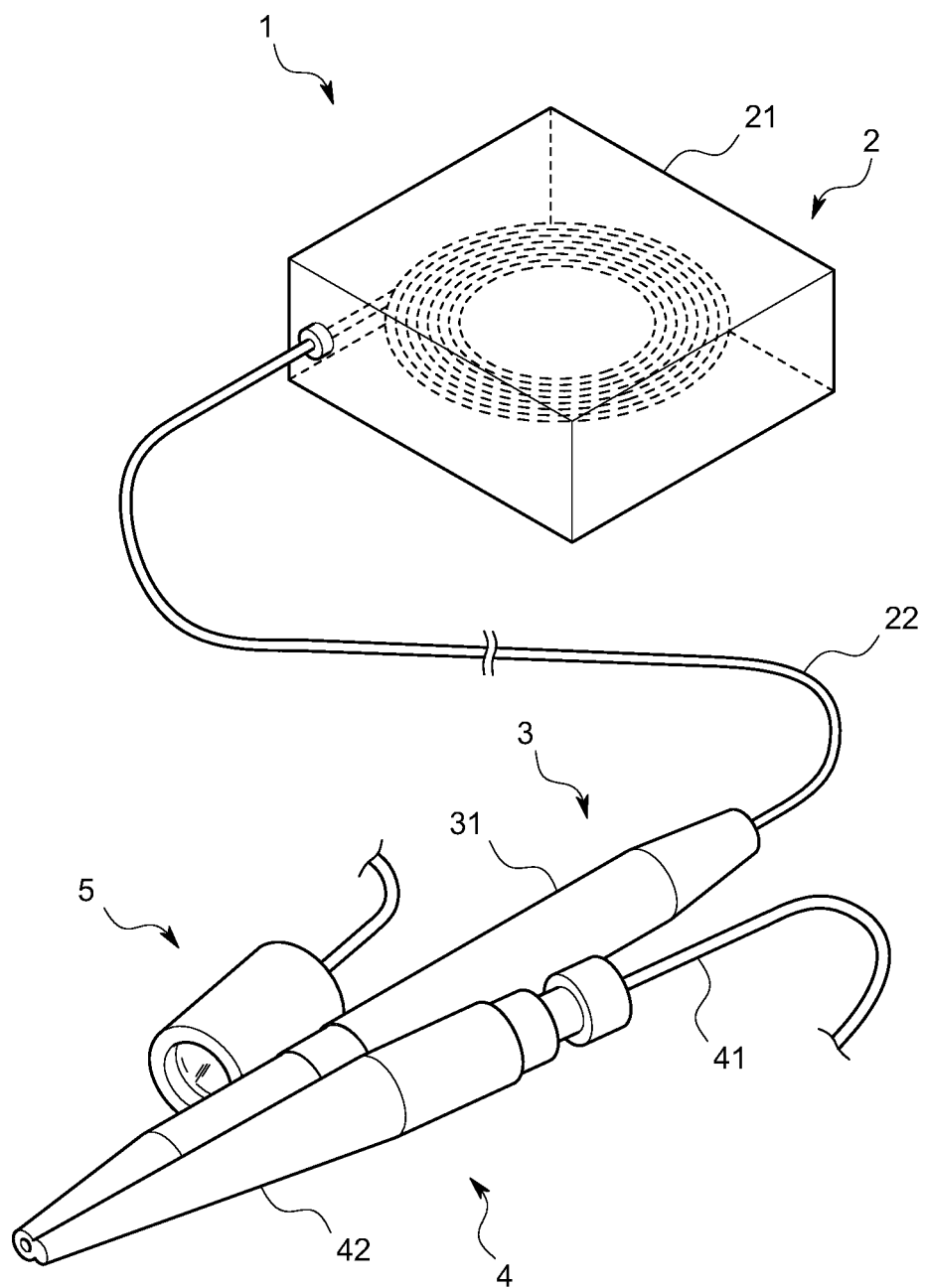
FIG. 1 is a schematic entire view of a bone cutting device according to one embodiment of the present invention.

As shown in FIG. 1, a bone cutting device 1 according to the present embodiment includes a laser device 2 including a base end of a disk type fiber laser 22 accommodated in a casing 21, a laser beam emitting part 3 provided at a tip of the disk type fiber laser 22 and containing a built-in optical system 32, a nitrogen gas jet part 4 for jetting nitrogen gas to a bone to be cut, and a distance sensor 5 for measuring a distance from the bone to be cut.

The laser device 2 includes the casing 21 and the disk type fiber laser 22 with its base end accommodated in the casing 21.

The casing 21 is a hollow case having space for accommodating the disk type fiber laser 22 inside thereof and has a compact size with its outer dimensions, for example, in a degree of width 60×depth 50×height 25 (cm).

The disk type fiber laser 22 is used in a state of winding the fiber laser which includes a fiber per se as a laser medium by adding a rare earth metal such as Er, Yb, or the like to an optical fiber so that space required for laser oscillation is remarkably reduced while an optical path length remains as it is. Since the actions of the fiber laser from excitation to oscillation and transmission are performed within an optical fiber, the fiber laser is strong against a shock and small in size and light in weight. The disk type fiber laser 22 is adapted to emit a laser beam L of 1000 to 1500 nm with a peak output of 10 to 70 W/cm$^2$. The disk type fiber laser 22 is preferably a single pulse laser from a viewpoint of suppressing heat generation of a cut position.

A tip portion of the disk type fiber laser 22 comes out to the exterior of the casing 21 and is connected to the base end of the laser beam emitting part 3.

Figure 2:
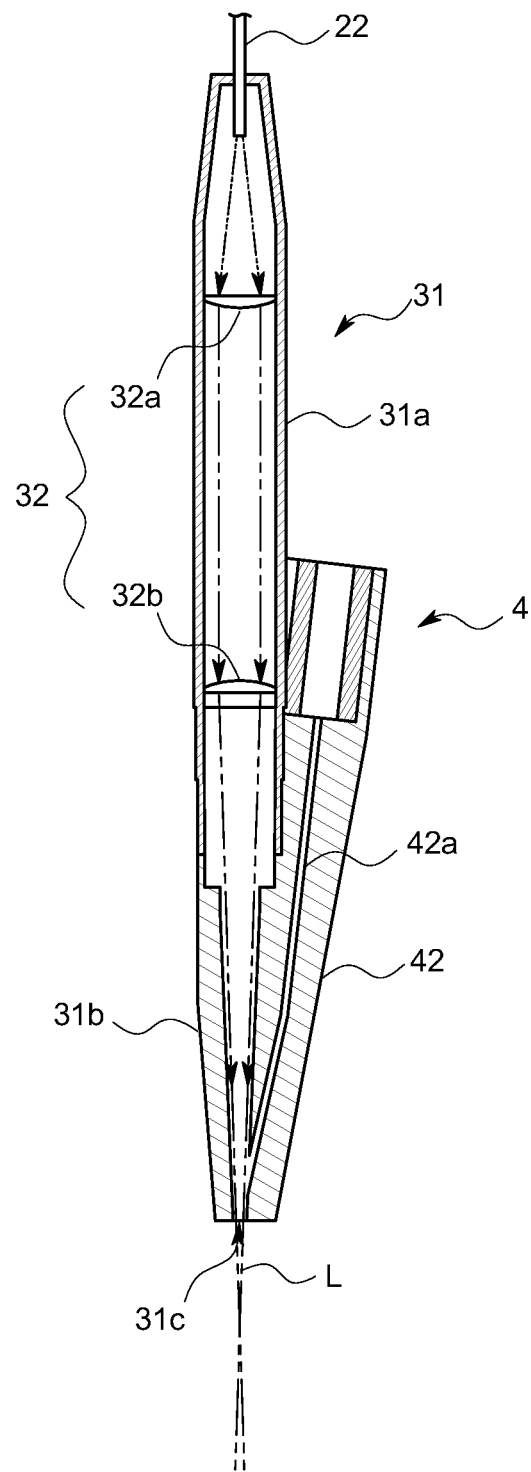
FIG. 2 is a schematic vertical sectional view showing an internal structure of a laser beam emitting part and a nitrogen gas jet part in the embodiment.
Figure 3:
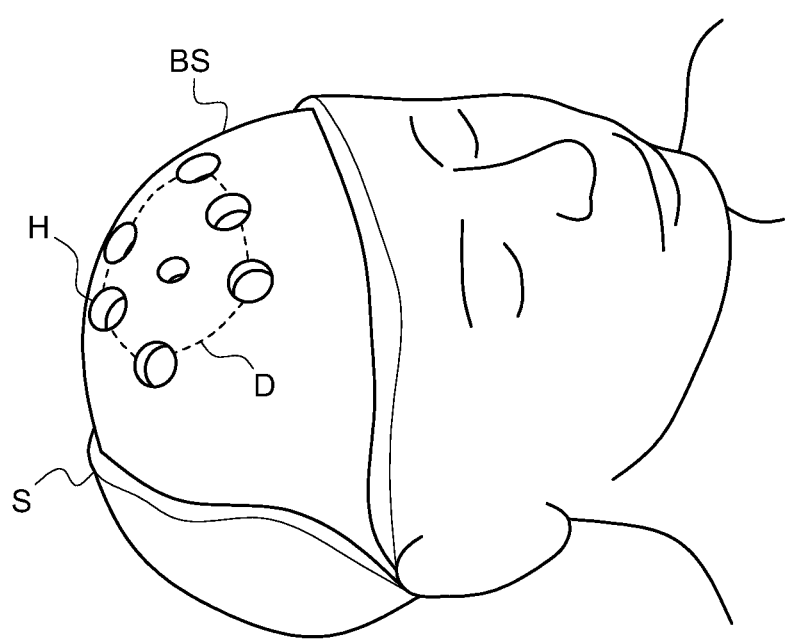
FIG. 3 is a diagram showing an outline of conventional craniotomy.

As shown in FIG. 2, the laser beam emitting part 3 is adapted to emit the laser beam L, which is introduced through the disk type fiber laser 22, from an emitting port 31c provided at a tip end thereof, and the laser beam emitting part 3 includes a body 31 and the optical system 32 accommodated in the body 31.

The body 31 is an elongated hollow body and is provided with a cylindrical grip part 31a and a taper shaped light shielding pipe 31b, and has a size and weight in a degree that an operator can grip side peripheral surfaces of the grip part 31a by one hand to operate the bone cutting device. And a connection port for connecting itself to the tip of the disk type fiber laser 22 is provided at the base end thereof, and the emitting port 31c for injecting outside the laser beam L outputted from the tip of the disk type fiber laser 22 and passed through the inside of the body 31 is opened at the tip portion thereof.

The optical system 32 includes a collimating lens 32a for collimating the laser beam L emitted and expanded from the disk type fiber laser 22 and a converging lens 32b for converging the laser beam L, which are arranged in series from the laser beam L incidence side in this order. As the lens 32b, for example, a planoconvex lens, an achromatic lens, and an object lens and the like can be used and a focal distance f thereof is 2 to 100 mm.

The nitrogen gas jet part 4 is adapted to jet nitrogen gas of 2 to 15 atmosphere to a bone to be cut and cool the bone to thereby suppress the thermal denaturation, and it is connected to a nitrogen gas supply source (not shown) via a tube 41 and includes a body 42 having a gas flow passage 42a formed inside thereof.

As shown in FIG. 2, the light shielding pipe 31b of the laser beam emitting part 3 and the body 42 of the nitrogen gas jet part 4 are integrally formed and the inside of the light shielding pipe 31b is communicated with the gas flow passage 42a of the nitrogen gas jet part 4 in the vicinity of the tip thereof so that the nitrogen gas supplied from the nitrogen gas supply source is jetted to the outside from the emitting port 31c provided at the tip of the light shielding pipe 31b together with the laser beam L.

The distance sensor 5 is adapted to measure a distance from a bone to be cut and to adjust the gripping position of the laser beam emitting part 3 in a manner that, for example, a focus of the laser beam L is positioned at a center of a bone marrow of the bone in the case where the bone is completely cut and that the focus of the laser beam L is positioned at a center of the bony tissue in the case where only the bony tissue is exfoliated. However, in the case where the center of the bone marrow is set as a target focal position, it is possible to cut only a bone without damaging the peripheral tissues even if the laser beam L is defocused in a degree of 20 mm in the upper and lower sides. The distance between the emitting port 31c of the laser beam emitting part 3 and the bone to be cut is preferably in a degree of 2 to 20 mm and more preferably around 5 mm so that the nitrogen gas can cool a cut region efficiently.

As a distance sensor 5 like this, for example, an optical type using an infrared semiconductor laser as a light source is used.

Next, a method of performing craniotomy using the bone cutting device 1 constructed as described above is explained.

Initially, a medical practitioner incises a scalp and exposes a cranial bone, and subsequently brings the tip of the laser beam emitting part 3 close to or in contact with the exposed cranial bone while measuring the distance by the distance sensor 5, and moves the laser beam emitting part 3 along an outline of the craniotomy range while the laser beam L of 1000 to 1500 nm is continuously (CW) or intermittently (pulse wave of 100 ns to 5 µs) emitted with a peak output appropriately selected according to a thickness of the bone to be cut within a range of 10 to 70 W/cm$^2$. Thus, only a cranial bone is selectively cut without damaging the other tissues, including a brain, at all. At this time, in order to cool a laser beam L irradiation portion and to blow away shavings of the bone, the cutting operation is performed while jetting the nitrogen gas in a degree of 0.4 MPa through the nitrogen gas jet part 4. In the craniotomy, it is not necessary to form a hole in the cranial bone beforehand.

Therefore, according to the bone cutting device 1 constructed like this, by irradiating with a laser beam L of 1000 to 1500 nm having a low absorptivity to water in a degree of 20 to 30% with a peak output of 10 to 70 W/cm$^2$, it is possible to selectively cut only a bone quickly at a speed in a degree of 2 mm/s without damaging peripheral tissues. For this reason, in the case of using the bone cutting device for craniotomy, it is possible to cut only a cranial bone quickly and take it off without damaging a brain only by one process of irradiating with the laser beam L without perforating the cranial bone after incision of the scalp.

Moreover, if a bone to be cut is irradiated with the laser beam L of 1000 to 1500 nm with a peak output of 10 to 70 W/cm$^2$, since the output of the laser beam L after penetrating the bone is degraded to a degree of about 30 W/cm$^2$ or lower, the peripheral tissues are not damaged at all. For this reason, it is not necessary at all to provide a member for intercepting the laser beam L between the bone and the peripheral tissues.

Moreover, in the craniotomy using the bone cutting device 1 according to the present embodiment, even if a patient's head is not firmly fixed as in the conventional manner, a bone piece can be cut out safely and precisely.

Further, since the bone is cut by irradiating with the laser beam L, a chipping allowance is very slight and physical breakage and deterioration of the cut-out bone piece are also little. For this reason, it is possible to re-join the cut-out bone piece as it is to the cut position even without using a fastener or the like.

Therefore, the craniotomy using the bone cutting device 1 according to the present embodiment as described above is by far less invasive with a light physical burden for a patient and dangers of a postoperative infectious disease and rejection are also low, compared to the conventional craniotomy using a mechanical instrument such as a drill, an electromotive coping saw, a chisel or the like. Also, since the craniotomy can be carried out with reduced induction factors of malpractice, physical and mental burdens for a medical practitioner can be also remarkably reduced.

Moreover, since the bone cutting device 1 according to the present embodiment is provided with the nitrogen gas jet part 4, thermal denaturation of a bone to be cut can be suppressed more effectively. When a bone is cut by a bone saw, the thermal denaturation is prevented using flowing water in many cases, and in this case, the recovery task of the water is complicated, whereas in the present embodiment, since the bone is cooled with nitrogen gas, such a recovery task is unnecessary, and further in the case of using water, the laser beam L is possibly absorbed and also reflected by the water per se, whereas in the case of using nitrogen gas, such a problem does not arise.

Further, since the bone cutting device 1 according to the present embodiment is provided with the distance sensor 5, the focal position of the laser beam L can be precisely controlled so that a highly precise positioning can be performed and the bone cutting operation can be further conducted with high safety. For this reason, the burdens for both of a patient and a medical practitioner can be reduced.

Furthermore, in the present embodiment, since the disk type fiber laser 22, which is formed to be a disk type by winding the fiber laser, is used as a light source, it is possible to arrange a plurality of semiconductor lasers for excitation on the side having a large area so that high intensity excitation and a high power output can be realized.

It is noted that the present invention is not limited to the embodiment mentioned above.

For example, a light source in the present invention is not limited to a disk type fiber laser as long as a laser beam L of 1000 to 1500 nm is emitted and, for example, a Nd:YAG laser and the like can be also used.

The laser beam emitting part 3 may not be directly gripped by an operator and, for example, the laser beam emitting part 3 gripped by a robot arm may be remote-controlled by an operator.

Moreover, the use of the bone cutting device according to the present invention is not limited to craniotomy, and it may be applicable to any use as long as a process of cutting a bone is included and it may be applicable to any use other than that in a medical field.

In addition, it is needless to say that the embodiments and modified embodiments described above may be partly or entirely combined appropriately and various changes and modifications may be made within a range unless deviated from the intent thereof.

INDUSTRIAL APPLICABILITY

By applying the present invention, since a bone can be cut by low invasive means, a physical burden for a patient can be remarkably reduced and a danger of occurrence of a postoperative infectious disease can be also reduced. Further, since damage and deterioration of a bone piece are little, it is possible to re-join the bone piece to the cut position even without using a fastener or the like. In addition, the burden of a bone cutting operation for a medical practitioner can be also remarkably reduced.

REFERENCE CHARACTERS LIST

1 . . . . Bone cutting device
22 . . . . Disk type fiber laser

The invention claimed is:
1. A bone cutting device configured to cut a bone by irradiation of the bone with a laser beam, comprising:
a body forming an emitting port;
a light source for emitting a laser beam of 1000 to 1500 nm with a peak output of 10 to 70 W/cm$^2$, wherein the light source is configured to emit the laser beam through the emitting port to cut the bone by irradiating with the laser beam of 1000 to 1500 nm with the peak output of 10 to 70 W/cm$^2$; and an inactive gas jet part configured to receive inactive gas and jet the inactive gas through the emitting port to the bone to be cut.

2. The bone cutting device according to claim 1, wherein the light source is a fiber laser which comprises an optical fiber including rare earth metal as a laser medium.

3. The bone cutting device according to claim 1 further comprising an inactive gas supply source to supply inactive gas to the jet part.

4. The bone cutting device according to claim 1 further comprising:
    a laser beam emitting part which is provided at a tip of the light source, and
    a distance sensor that measures a distance between the emitting port of the laser beam emitting part and the bone to be cut.

5. The bone cutting device according to claim 4, further comprising:
    an optical system configured to adjust a focal position of the laser beam based on the distance between the emitting port of the laser beam emitting part and the bone to be cut as measured by the distance sensor.

6. The bone cutting device according to claim 1, wherein a distance between the emitting port and the bone to be cut is in a range of 2 to 20 mm.

7. The bone cutting device according to claim 6, wherein the distance is around 5 mm.

8. The bone cutting device according to claim 6, wherein an output of the laser beam after penetrating the bone is degraded to a degree of less than about 30 W/cm$^2$.

* * * * *